(12) United States Patent
Hubregtse et al.

(10) Patent No.: US 10,814,096 B2
(45) Date of Patent: Oct. 27, 2020

(54) CATHETER ASSEMBLY

(75) Inventors: Marc Hubregtse, Rotterdam (NL); Johan Remmerswaal, Rotterdam (NL)

(73) Assignee: URECA B.V., Rotterdam (NL)

( * ) Notice: Subject to any disclaimer, the term of this patent is extended or adjusted under 35 U.S.C. 154(b) by 0 days.

(21) Appl. No.: 13/488,610

(22) Filed: Jun. 5, 2012

(65) Prior Publication Data

US 2012/0239073 A1 Sep. 20, 2012

Related U.S. Application Data

(63) Continuation of application No. 12/809,737, filed as application No. PCT/NL2008/050844 on Dec. 22, 2008, now Pat. No. 8,206,322.

(30) Foreign Application Priority Data

Dec. 20, 2007 (NL) .................................. 2001109

(51) Int. Cl.
*A61M 25/01* (2006.01)
*A61B 17/00* (2006.01)
(Continued)

(52) U.S. Cl.
CPC ....... *A61M 25/01* (2013.01); *A61B 17/00234* (2013.01); *A61B 17/22* (2013.01);
(Continued)

(58) Field of Classification Search
CPC .. A61M 2025/0197; A61M 2025/0081; A61M 25/01; A61M 25/0082;
(Continued)

(56) References Cited

U.S. PATENT DOCUMENTS 4,643,187 A * 2/1987 Okada .................... A61B 18/14
606/47
5,303,714 A * 4/1994 Abele et al. .................. 600/585
(Continued)

FOREIGN PATENT DOCUMENTS

JP 2005-270464 A 10/2005
WO 00/06242 A1 2/2000

OTHER PUBLICATIONS

International Search Report, dated Feb. 25, 2009, from corresponding PCT application.

*Primary Examiner* — Patrick Fernandes
(74) *Attorney, Agent, or Firm* — Foley & Lardner LLP

(57) ABSTRACT

A catheter assembly provided with a wire arranged therein to form a loop extending from near the effective end of the catheter for bypassing an occlusion in a vein/artery. This loop consists of two wire ends, one of which wire ends extends through the catheter to the control end thereof, while the other wire end is attached thereto, in close proximity to the effective end of the catheter. By varying the relative position of the loop wire end extending from the control end and the control end, the size of the loop and the pushability thereof at the effective end of the catheter can be determined. In this manner, the occlusion can be removed with precise control by the physician using two hands. In addition, the catheter is formed not only for the loop wire end extending through the catheter, but also for incorporating a guide wire and/or for contrast fluids.

19 Claims, 4 Drawing Sheets

(51) Int. Cl.
  *A61B 17/22*   (2006.01)
  *A61M 25/00*   (2006.01)
  *A61B 17/3207* (2006.01)
  *A61B 17/3205* (2006.01)

(52) U.S. Cl.
  CPC ... *A61M 25/0082* (2013.01); *A61B 17/32056* (2013.01); *A61B 2017/00252* (2013.01); *A61B 2017/00269* (2013.01); *A61B 2017/22044* (2013.01); *A61B 2017/22094* (2013.01); *A61B 2017/22095* (2013.01); *A61B 2017/320733* (2013.01); *A61M 2025/0081* (2013.01); *A61M 2025/0197* (2013.01)

(58) Field of Classification Search
  CPC ......... A61B 2017/22094; A61B 2017/320733; A61B 2017/22095; A61B 2017/22044; A61B 2017/00269; A61B 2017/00252; A61B 17/32056; A61B 17/22; A61B 17/00234
  USPC .................. 600/433, 434, 585; 604/164.13
  See application file for complete search history.

(56) References Cited

U.S. PATENT DOCUMENTS

| | | | |
|---|---|---|---|
| 5,387,219 A | | 2/1995 | Rappe |
| 5,522,819 A | | 6/1996 | Graves et al. |
| 5,716,321 A | * | 2/1998 | Kerin ................... A61B 1/0008 600/104 |
| 5,797,948 A | * | 8/1998 | Dunham ....................... 606/194 |
| 2002/0123698 A1 | | 9/2002 | Garibotto et al. |
| 2006/0206125 A1 | * | 9/2006 | Fogarty et al. ............... 606/159 |

\* cited by examiner

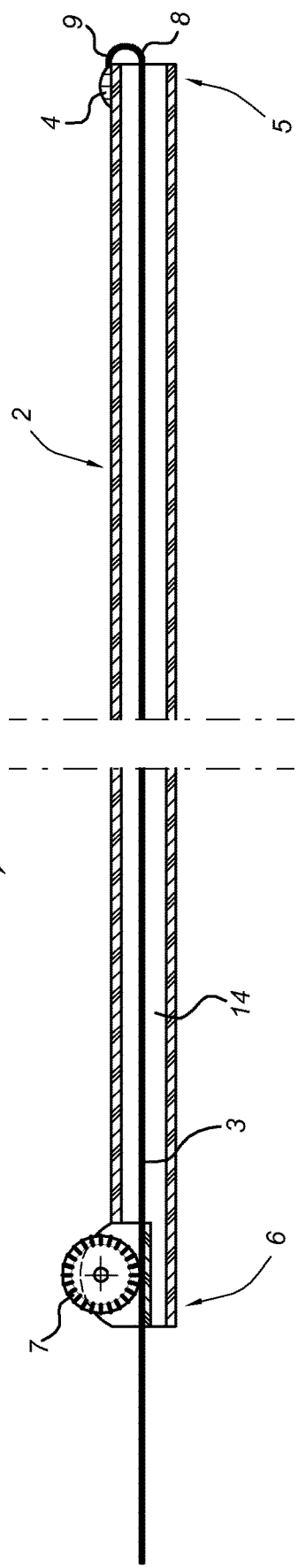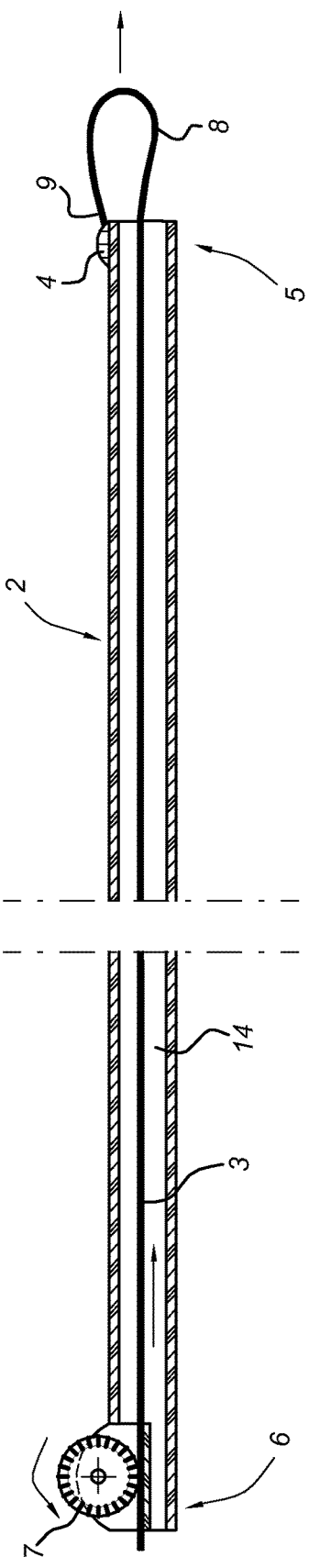

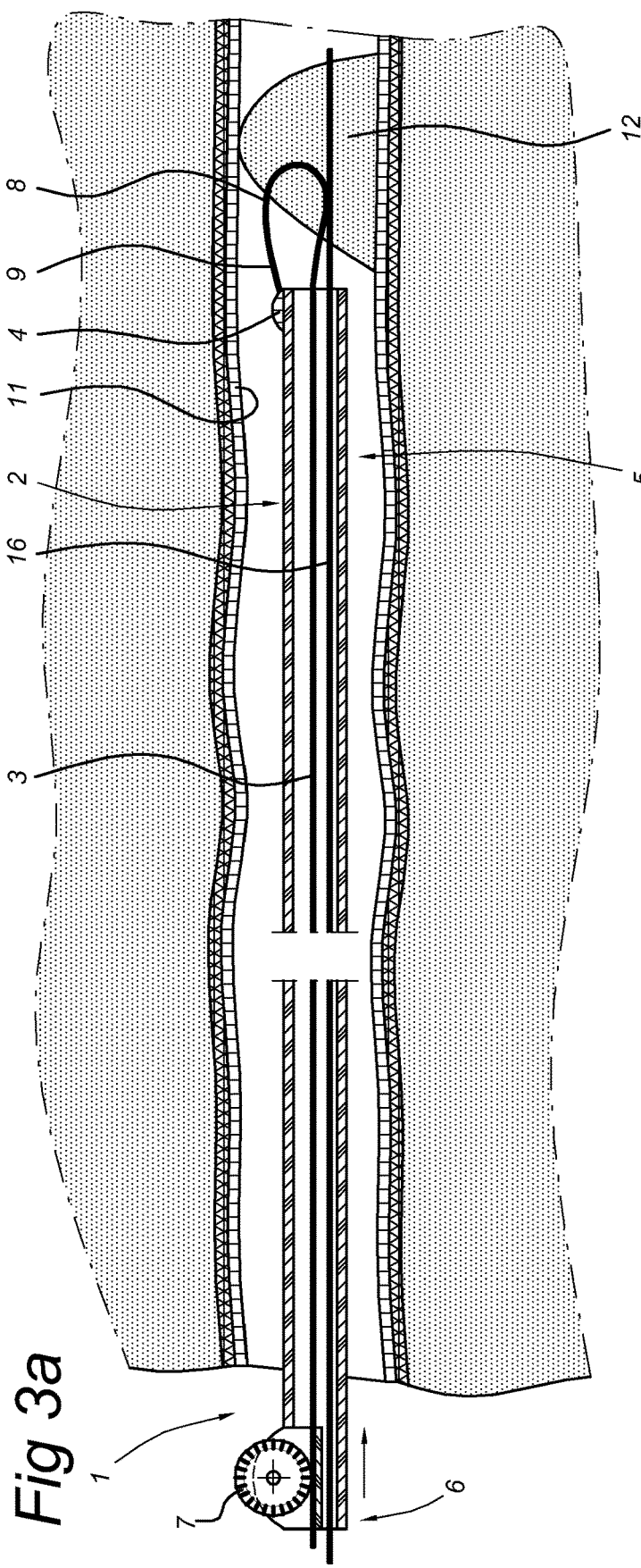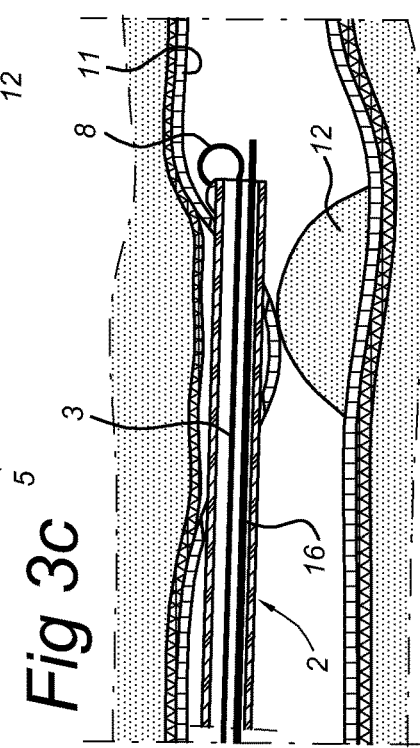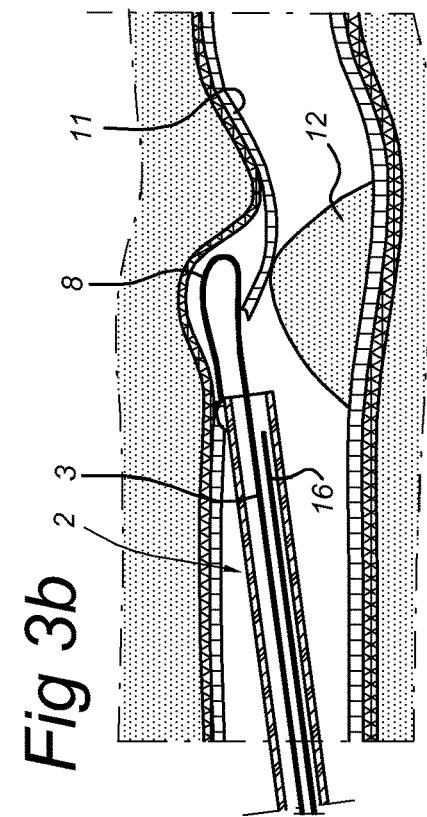

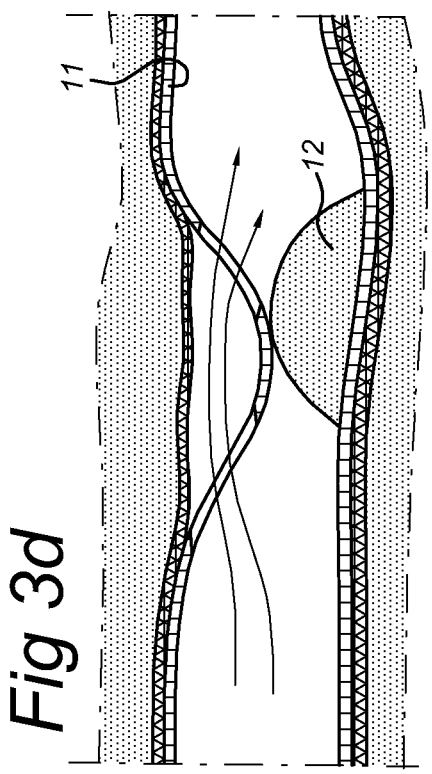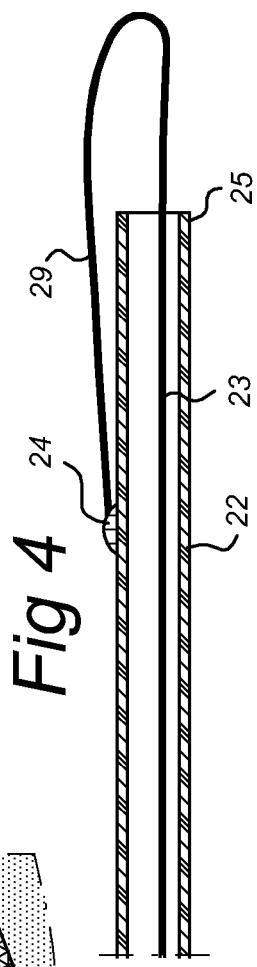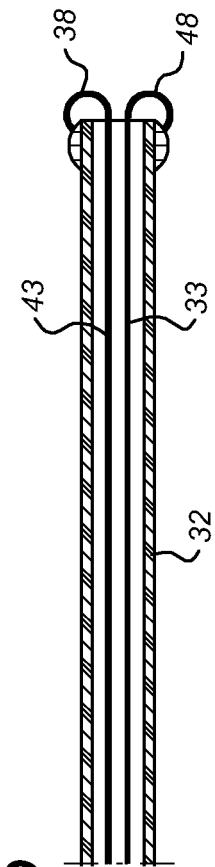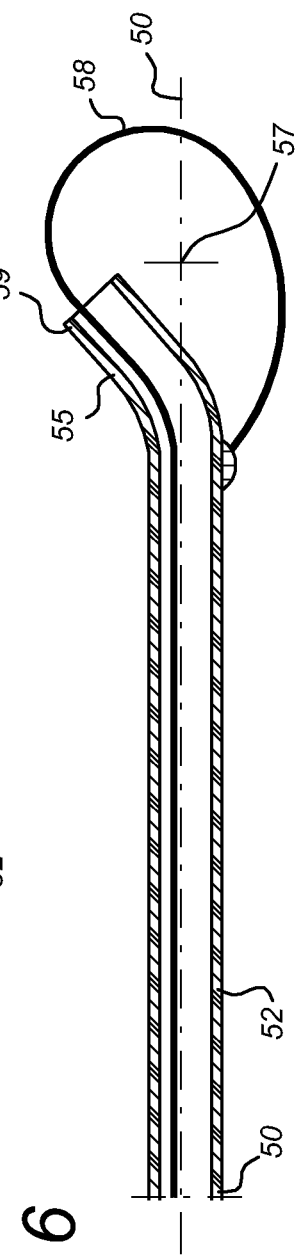

Fig 7
Fig 8
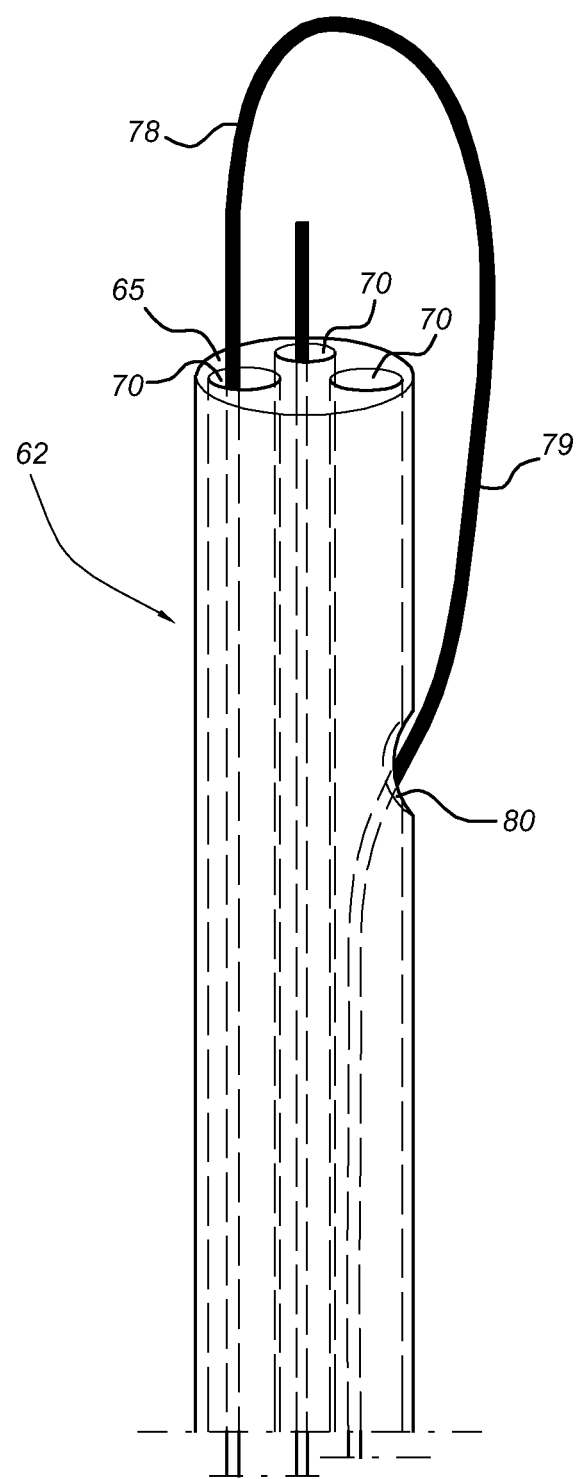
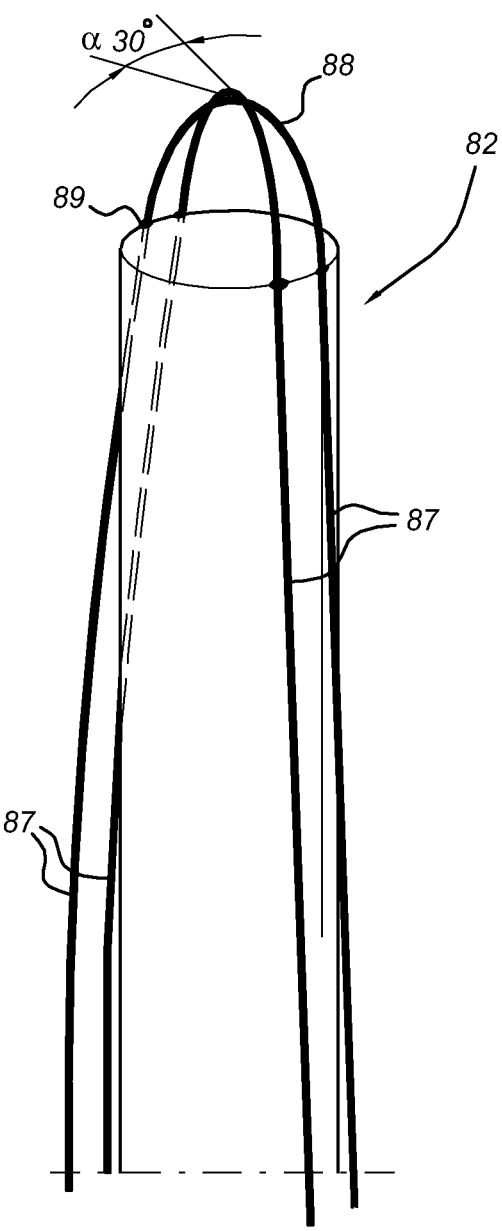

US 10,814,096 B2

CATHETER ASSEMBLY

CROSS REFERENCE TO RELATED APPLICATIONS

This application is a continuation of copending application Ser. No. 12/809,737 filed on Oct. 4, 2010; which is the 35 U.S.C. 371 national stage of International application PCT/NL08/050,844 filed on Dec. 22, 2008; which claims priority to Netherlands application 2001109 filed on Dec. 20, 2007. The entire contents of each of the above-identified applications are hereby incorporated by reference.

BACKGROUND OF THE INVENTION

The present invention relates to a catheter assembly according to the preamble of claim 1.

Such a catheter is generally known in the prior art and is used in percutaneous interventions in veins and arteries. For bypassing occlusions in veins/arteries, a catheter is used wherein a wire, preferably curved, extends outwards from the effective end, i.e. the end protruding farthest into the body of the living being. By manipulating the wire in relation to the catheter, an attempt is made to obtain a loop wherein an end of that wire is disposed within the catheter and a shorter end is disposed freely outside of the catheter. A bypass can be achieved by advancing the loop thus obtained forward in the direction of and subsequently through or past the occlusion. By advancing the control end more or less in the direction of the effective end of the long loop wire end that extends through the catheter, in relation to the catheter, the loop size can be enlarged or reduced. However, such action requires an exceptional degree of experience, as well as an accurate and sensitive hand. After all, on the one hand, the loop needs to have a certain optimal size in order to engage the occlusion, which can be achieved by varying the relative position of the loop wire end in relation to the control end of the catheter. Conversely, the relative position of the effective end of the catheter and the loop in relation to the occlusion is of importance. In practice, this means that two types of movements must be coordinated, namely increasing/reducing the size of the loop and the positioning of the loop or effective end of the catheter in relation to the occlusion. Such coordination is necessary in order to generate a controlled pressure in order to bypass the occlusion. Moreover, forming and maintaining a loop is an obstacle for those inexperienced in the art.

This is why this method for removing the effect of occlusions in veins/arteries by approaching these with a wire loop and by forming a bypass is not widely accepted. Moreover, a number of actions are required in order to achieve the desired situation. First, a guide wire is inserted into the respective vein/artery and the catheter is then advanced along the guide wire to the desired location where the occlusion is located. Subsequently, the guide wire is removed and the loop-forming wire is inserted through the catheter. To achieve this, the loop-forming wire must possess certain properties in order to be advanced through the internals of the catheter, after which the loop can actually be formed.

Moreover, the technique described above only applies to veins/arteries with a relatively large diameter. In smaller veins/arteries, it is not possible in this manner to form a loop and therefore not possible to bypass an occlusion.

A catheter is known from U.S. 2002/1023698, which can be provided with a snaring device. This snaring device is formed in order to capture other guide wires to form a connection in this manner between two adjacent vessels. This device is intended, in particular, for coronary applications.

JP2005-270464 describes a device for the removal of debris from blood vessel walls. To this end, a catheter is introduced and a scraping loop is advanced from the free end thereof and advanced along the wall of a vessel in order to remove fine particles therefrom. Superfluous material is removed by suction through the internals of the catheter.

SUMMARY OF THE INVENTION

The object of the present invention is to eliminate the disadvantages associated with the prior art and to provide an improved method for manipulating a loop/catheter assembly, enabled by providing an improved catheter or improved catheter assembly. This object is achieved in a catheter assembly having the features of claim 1. According to the present invention, as in the prior art, the one loop wire end in the catheter is guided; however, there is no longer question of another free loop wire end. The other loop wire end is supported by the catheter. This support can be achieved in any conceivable manner but will always result in the fact that it is much easier to form and maintain the loop, thus greatly simplifying the operation. After all, the formation of the loop by the support is no longer a problem and the person operating the loop can fully concentrate on the action to be performed of bypassing the occlusion with the loop. By using a combination of a rigid catheter and a rigid loop wire material, a separation action can be performed in a forward direction, i.e. in the longitudinal plane of the catheter-loop. Depending on the condition of the patient, the operating force will apply for bypassing an occlusion. Due to calcification, it is possible that a substantial force needs to be exerted by the front side of the loop. In that case, the loop thus chosen must be small in order to make the rigidity of the assembly of loop and catheter as high as possible. The force exerted when passing/bypassing the occlusion may vary from several grammes and preferably tens of grammes, to several hundred grammes of force. This rigidity is significantly higher than the rigidity required only for introducing a catheter in a vein/artery, for example, for performing the operations known in U.S. 2002/1023698 and JP 2005-270464. After all, in the case of calcification, this presents a substantial obstacle for the further advancement of the catheter with the loop.

More specifically, according to the present invention, the rigidity of the catheter, and in particular the effective end of the catheter, is greater than the rigidity of the preceding loop. This relates in particular to resistance to kinking. Accordingly, pressure can be exerted upon the tissue in a controllable manner so that, when greater loads are exerted, the loop deforms, not the end of the catheter. This distinguishes the present catheter from the catheters known from the above publications U.S. 2002/1023698 and JP 2005/270464, which are specifically formed for exerting a pulling force.

According to a particular embodiment of the invention only channels for incorporating wires are disposed in the catheter, such as the loop wire end described above and guide wires. Possibly, a channel may also be present exclusively for the delivery of a medium, such as a contrast fluid. Another example of a channel for the delivery of a medium is a channel for delivering gas/air in order to operate any dilatation means. This means that the catheter is not provided with a channel for the removal of material by suction. Such a channel for the removal of material by suction is relatively large in size in order to permit the passage of debris particles and is formed in such a manner that this does not collapse under vacuum pressure.

Moreover, with the present invention, it is also possible to bypass occlusions in smaller veins/arteries by pushing and by separation. If necessary, a cutting operation may also be performed. After all, the loop can also be formed in smaller veins/arteries. Examples of veins/arteries with a smaller diameter are the coronary arteries.

As indicated above, the support of the other loop wire end can be achieved in any other conceivable manner. Accordingly, it is possible that the other loop wire end extends over a considerable length, either externally parallel or internally parallel and adjacent to the catheter. The other loop wire end may even extend to the exterior of the body of the living being in which the operation is performed. A further possibility is that both loop wire ends extend through the catheter while the other loop wire end may also extend to the control end or up to yet another position.

Another possibility is that the other loop wire end is attached to the catheter. This attachment can be formed at the effective end but it is also possible for this attachment to be made to the catheter at another location, either internally or externally. Moreover, it is possible to form this attachment in such a manner that the attachment is rendered redundant when the loop is manipulated in a specific way. It is possible, for example, by exerting traction on the one loop wire end, to ensure that the other loop wire end breaks off from the catheter so that the resulting wire can be used, for example, as a guide wire. According to a particular embodiment of the invention, the end of the broken off loop wire is rounded, i.e. formed with a soft-tip in order to prevent tissue damage.

A further possibility is that the other loop wire end enters the catheter through a laterally formed aperture, where it may be either attached or remain unattached. In the event the other loop wire end is not attached, this may extend to the control end of the catheter. A lateral aperture as such can also be used in combination with the above-described catheter through which a piercing needle can be guided.

In all the cases described above a loop can be easily formed and it is possible to modify the size of the loop by the relative movement of the control end of the catheter and the loop wire end extending therefrom. That is to say that, in the alternative embodiment wherein the loop wire end is fixated in relation to the catheter, one of the control parameters according to the state of the art is no longer required, namely that of the manipulation of the loop wire end.

The one loop wire end will generally extend through the catheter to the effective end thereof. By varying the end extending from the operative end of the catheter, the size of the loop can be changed, as described above. However, it is also possible to have this one end supported by the catheter by all means described above for the other end. One possibility is to fixate both the one end and the other end to the end of the catheter, the use of the previously described lateral aperture etc. In the first case, wherein both ends of the loop wire are firmly attached to the catheter, the loop wire may have any conceivable embodiment, as long as it provides for the function of bypassing an occlusion. After all, since the dimensions thereof no longer need to be varied during use, it is also possible to apply the loop wire more specifically to perform other functions. One example is a cutting feature. Moreover, a cutting feature as such may also be present in a loop wire which is moveable in relation to the catheter. Such a cutting feature is preferably incorporated in the loop wire and in a normal operating position, i.e. in a normally required loop, it will not be active because it will be located within the catheter. However, by moving the loop wire further from the catheter, such a cutting member of the loop wire can become effective for separating and/or cutting away tissue in difficult cases. This is particularly important for re-entering the original vein/artery after bypassing the occlusion.

It appeared that it is possible, by applying the invention in a very precise manner, to determine the size of the loop and thus the effectiveness thereof. Moreover, it is possible to not only accurately determine the size of the loop, but also the position thereof or the position of the effective end of the catheter. The physician can operate the catheter assembly, consisting of the above described catheter and loop wire, very precisely with two hands. This, as opposed to the prior art where, in fact, a 'third' hand is required. It is also possible, with the aid use indicator means, to determine the displacement of the one loop wire end relative to the catheter so that an accurate prediction can be made of the position of the other loop wire end and thus the size of the loop. This value is a measure for the pushability of the assembly. It is also possible using other techniques, to indicate to the use the position of the support or the support points of the loop in relation to the catheter.

It is possible to bypass an occlusion by varying the size of the loop. A small loop, may have a relatively high strength/rigidity, but has a limited range in relation to the tissue to be separated. A larger loop can be advanced further, but has a lower mechanical strength. By continuously varying the size of the loop during the further advancement of the effective end of the catheter, an occlusion can be bypassed quite effectively. The principle of bypassing the occlusion is consistent with what is known as such, i.e. to create an opening by separating the vessel wall in different tissue layers. However, the method of bypassing the occlusion by engaging the vessel wall does not form any part of the invention and the accuracy of that which is described above is not relevant to the validity of the patent.

According to a particular embodiment of the present invention, the catheter assembly, comprising catheter and single loop wire end disposed therein, is embodied in such a manner that there is sufficient space therein to incorporate a guide wire and/or to permit the passage of contrast fluid.

By enabling a guide wire to be guided through the catheter, after the guide wire is attached, the catheter can be advanced in one step, together with the loop wire end already attached thereto, and of course with the other loop wire end attached to the effective end of the catheter, along the guide wire to beyond the occlusion. Subsequently, this can be readily followed by bypassing the occlusion. This means that the required step in the prior art, of first introducing the catheter, followed by the insertion of the loop wire, is no longer necessary. This also means that the position of the loop can be determined more accurately. After the optional removal of the guide wire, a contrast fluid can be delivered which is made visible, for example, by means of X-ray techniques, thus enabling the close monitoring of the actions performed in the veins/arteries.

The above described catheter is a catheter and catheter assembly based upon an embodiment with a single loop. However, due to the simplicity with which such a loop can be achieved, it is possible in the proximity of the effective end of the catheter to attach more than one loop, such as two wire loops, which lie in two mutually opposing directions and which are either jointly or individually controllable. The relative angle depends on the desired characteristics and lies, for example, between 15 and 45° for the simple bypassing of an occlusion.

In addition, the catheter end proximate to the effective end is preferably somewhat curved and directed outwards, i.e. deviating from the longitudinal axis of the catheter so that a wire loop can be caused to form, the centre of which lies on the extension of the above mentioned centre line.

The mechanical properties of the catheter assembly, comprising catheter and loop wire, are dependent on the individual mechanical properties of the catheter and loop wire. However, the loop wire may provide a reinforcement of the catheter. This is particularly true if the loop wire is disposed relatively tightly and closely within the catheter. This can be achieved, for example, by using the channels present in the catheter for incorporating the loop wire.

The maximum pressure which may be exerted on the end of the loop when bypassing an occlusion, i.e. the so-called "pushability", depends on the size of the loop, the rigidity of the loop wire and the rigidity of the catheter used. In principle, it will always be an objective to use an assembly which is as rigid as possible so that it can be used as efficiently as possible. In all cases, however, the risk of tissue damage must be avoided. Accordingly, a greater pushability will be more acceptable in the case of an occlusion in an artery in a leg than in the treatment or bypassing of an occlusion in a coronary artery. It will be understood that the pushability is less in a large loop than in a smaller loop in the same catheter and loop-wire assembly. From the above it will be apparent that the physician will choose an assembly with a certain pushability, depending on the treatment to be performed. All these possibilities of variation or pushability of the strength are possible because one of the loop wire ends is located in a precisely defined position in relation to the control end of the catheter.

According to a further advantageous embodiment, measures have been taken to enable the in situ insertion of a balloon or other dilatation means directly after bypassing the occlusion and to widen the opening thus obtained.

The movement back and forth of the loop wire end which extends through the catheter can be accurately controlled from the control end of the catheter. If necessary, a scale gradation can be provided indicating the advancement of the loop wire end in the catheter so that an accurate prediction can be made regarding the size of the loop at the effective end of the catheter.

The invention also relates to a method for passing/bypassing an occlusion in a vein/artery, comprising the introduction of a catheter up to the occlusion, the advancement of a loop at the effective end of said catheter comprising a loop wire end extending to the control end of said catheter, the loop being advanced in the direction of said occlusion and the passing/bypassing past said occlusion by the relative movement of loop wire and catheter, wherein the other end of said loop is supported by said catheter. The vein/artery described here may be any vein or artery in a living being. The invention has been successfully implemented in the bypassing of occlusions in limbs such as legs, but can also be performed on other (coronary) veins/arteries. If necessary, a stent may also be subsequently placed. Such a stent may, for example, be pushed along a guide wire which functioned originally as a loop wire.

The rigidity of the catheter is understood to mean the stiffness of the catheter itself, without the loop wire end.

BRIEF DESCRIPTION OF THE DRAWINGS

The invention will be described in more detail below with reference to an exemplary embodiment shown in the drawing, in which:

FIG. 1 shows, highly schematically, a catheter according to the present invention with a loop wire in a first position;

FIG. 2 shows the catheter according to FIG. 1, with the loop wire and/or loop in a second position;

FIG. 3a-d shows, highly schematically, the introduction of the catheter assembly according to the present invention through a vessel over a guide wire and the bypassing of an occlusion;

FIG. 4 shows a first alternative embodiment of the invention;

FIG. 5 shows a second alternative embodiment of the invention;

FIG. 6 shows a further alternative embodiment of the invention,

FIG. 7 shows a fourth alternative embodiment of the invention, and

FIG. 8 shows a further alternative embodiment of the invention.

In FIG. 1, the catheter assembly according to the present invention is indicated in its entirety by the numeral 1. This consists of a conventional hollow catheter 2 which can be advanced as a tube through, for example, a vein/artery. It will be understood that the lumen normally present in a catheter is also present in this case, but not illustrated for reasons of clarity. This also applies to other details of the catheter which are omitted for reasons of clarity. As will be apparent in FIG. 1, an attachment 4 is provided at the effective end 5 where the loop wire end 9 of a loop 8 is attached. The other loop wire end is indicated by the numeral 3 and extends along the entire length of the catheter past the control wheel 7 at the control end 6 of the catheter. By rotating the wheel, the loop wire end 3 can be moved back and forth and the loop 8 will be made smaller or larger. By providing a scale gradation at the location of the control wheel, the movement of the loop wire end 3 can be determined and thus the size of the loop 8. Instead of the single control wheel 7 shown here, two opposing wheels may be present, between which loop wire end 3 can be guided.

FIG. 2 shows an example of such an advancement of the loop wire 3 in the direction of the effective end of the catheter and this shows that this results in an increase in the size of loop 8 (i.e., a first diameter of the loop 8 that runs along a longitudinal axis of the catheter 2 increases relative to a second diameter of the loop 8 that runs perpendicular to the longitudinal axis of the catheter 2).

The catheter 2 is formed in such a manner that space is still available in the lumen 14 thereof for a guide wire 16, in addition to the loop wire end 3.

FIG. 3 a-d shows how a guide wire 16 is first inserted through a vein/artery 11 and is then followed by the introduction of the catheter assembly 1 according to the present invention. This catheter assembly according to the present invention, already comprises the loop wire ends 3 and 9 when introduced, wherein loop wire end 9, for example, is attached to attachment position 4 at the effective end 5 of the catheter 2. This means that, as opposed to the prior art, it is no longer necessary to insert the loop wires after first removing the guide wire after the catheter has reached its target location. This target location is indicated schematically in FIG. 3 by the numeral 12, i.e. the numeral 12 indicates an occlusion.

By pressing the loop wire end 3 forward and by moving back and forth, space is created for passing/bypassing the occlusion by pushing aside or removing the tissue. If necessary, cutting of the intima may then take place, after which the separation of intima and media can be performed. The front of the loop 8 has a size that matches the (expected)

encountered resistance to the tissue to be bypassed. By simultaneously manipulating the catheter, the position of the loop in relation to the catheter and thus the occlusion button can be adjusted.

FIG. 3d shows the final situation in which the occlusion 12 is fully bypassed.

The combination of the catheter and loop wire extending therefrom determines the "pushability" of this assembly. This "pushability" is relatively high for a small loop and a relatively rigid catheter and is lower in a larger loop and/or less rigid catheter. These factors can be varied depending on the desired application.

The rigidity is determined by the choice of catheter.

With the present invention, it is possible, once the catheter assembly 1 is positioned at the occlusion 12, to bypass the occlusion by increasing and reducing the loop 8 in combination with a back and forth movement of both the loop and the active end 5 of the catheter, if necessary, by using a variably adjustable pressure rigidity of the entire catheter assembly by variation in the size of the loop. The protruding length of the loop may vary from zero to several centimeters. The displacement distance of the loop wire end 3 will be twice that length. This can be sensed quite accurately by the physician and is also recorded by the displacement of the loop wire end 3 at the control end 6 of the catheter. Of course, this can be supported by delivering a contrast fluid through the catheter, with or without the presence of the guide wire 16, and by making the contrast fluid visible, for example, by means of X-ray techniques.

With this invention, it is possible for less experienced medically trained persons to bypass an occlusion in a vein/artery so that such an action can be performed more frequently with all positive benefits as a result thereof.

After (partially) moving the loop with the catheter past the occlusion the opening thus obtained may be fixated and dilatated with the use of a balloon or other such dilatation means. The balloon may be inserted with the use of a balloon catheter, thus eliminating the need to re-insert the guide wire. After all, this remained present during the process of removing the occlusion with the catheter assembly according to the present invention. However, it is also possible to form the catheter assembly according to the present invention in a such a manner that this is/can be provided with a balloon.

According to a particular embodiment of the invention, the loop wire end 9 can be broken at attachment position 4 by pulling the wire end 3 tightly (to the left). In particular, the free end thus formed is rounded (soft tipped). In this way, wire 3, 8, 9, for example, can act as guide wire without the risk of damage to tissue. With this embodiment, it is possible to provide the attachment position of the wire not in the proximity of the catheter but more towards the inside, in the lumen thereof.

FIG. 4-8 shows, schematically, further alternative embodiments of the invention.

FIG. 4 shows a hollow catheter 22 with loop wire end 23, which, in principle, can be applied in the same manner as described above. However, the other loop wire end 29 is not attached at the effective end 25 of the catheter, but extends over some distance on the outer side of the catheter. Accordingly, it is possible that the other loop wire end 29 is attached to the catheter 22 at position 24. However, it is also possible that the other loop wire end 29 is not attached to the catheter, but only supported by the catheter. In principle, it is even possible that the other loop wire end 29 extends up to the control end.

A further alternative embodiment is shown in FIG. 5, in which two loop wire ends 33 and 43 are present in the catheter 32 which can be either jointly or individually controlled by the control end (not shown). In this manner, two loops 38 and 48 are caused to form. In this case, these are shown lying in one plane, but it is also possible for these to be positioned upright and/or that they partially enclose each other. For the purpose of controlling the loop wire ends 43 and 44, these may have a different color so that a clear distinction can be made between the formation of the loops 38 and 40.

FIG. 6 shows a catheter 52, the effective end 55 of which is slightly curved in relation to centre line 50. This will ensure that axis 57 of loop 58 lies on centre line 50. As a result, the pressure generated in the catheter assembly in the extension of the centre line thereof is exerted on the tissue without any component resulting in the lateral direction, which makes operation of the assembly easier. The end 59 of the catheter that deviates from the center line can be used, when there is no loop or only a very small loop, to precisely generate and exert a lateral force component.

If a catheter is used in combination with a loop to bypass an occlusion and to form a new passage in a vein/artery, a group of assemblies as described above may be used, commencing first with the relatively weak catheter assembly, i.e. with a catheter assembly of which the effective end is relatively non rigid, and the loop wire of which also has a relatively low strength. Should it become apparent that the desired result cannot be achieved in this manner, then another catheter assembly can be used which is somewhat more rigid.

FIG. 7 shows a further alternative embodiment of the invention, wherein the catheter 62 is provided with a number of channels or lumen 70. One of these channels 70 functions the purpose of guiding a loop wire for causing the formation of a loop 78. The other end of the loop wire 79 is guided back into the catheter through an aperture 80. This aperture 80 lies at some distance from the effective end 65 of the catheter. The other channels 70 can be used for a guide wire, for example, an additional loop wire or dilatation means such as a balloon. Due to the presence of the channels 70, the respective wires are incorporated relatively tightly and contribute substantially to the rigidity of the catheter and wire assembly.

The loop wire end 79 can be attached in close proximity to the aperture in the internals of the catheter or extend towards the control end thereof. The aforementioned options are also possible.

FIG. 8 shows an embodiment of the invention wherein the catheter 82 has two loop wires 88 crossing each other. The relative angle is indicated by a and is 30° in this exemplary embodiment. The ends of the loops are indicated by 89 and are firmly attached to the end of the catheter. Following this attachment, the loop wire ends 88 extend parallel to the catheter and these wire portions are indicated by 87. By pulling the control end of one of the wires 87, the catheter will bend and thus provide for the further manipulation thereof. The angle of 30° is preferred for bypassing occlusions. An angle of approximately 90° is preferred for enabling the maneuverability of the control end with the wire portions.

After reading the above, persons skilled in the art will be readily aware of alternative embodiments of the invention and these lie within the scope of the appended claims. In particular, reference is made to the combination of the above mentioned properties for the specific alternative embodiments which, of course, may also be applied in other alternative embodiments.

The invention claimed is:

1. A catheter assembly for passing or bypassing an occlusion in veins or arteries, comprising:
   a hollow catheter;
   a loop wire extending through the hollow catheter, the loop wire having a first loop wire end extending rearwardly from a control end of the hollow catheter and a second loop wire end supported on and extending forwardly from an operative end of the hollow catheter, the loop wire being arranged to be moved rearwardly and forwardly with respect to the hollow catheter,
   wherein a rigidity of the hollow catheter and the loop wire are such that a moveable part of the second loop wire end extending forwardly from the operative end of the hollow catheter forms a cutting loop,
   wherein an entirety of the cutting loop remains forward of the operative end of the hollow catheter,
   wherein the cutting loop is arranged to cut or part tissue at a distal cutting edge portion positioned at a distal tip of the cutting loop in a direction along a longitudinal axis of the hollow catheter, and
   wherein a rigidity of the cutting loop is sufficient to exert a pushing force from several grams to several hundred grams.

2. The catheter assembly according to claim 1, wherein a rigidity of the operative end of the hollow catheter is greater than a rigidity of the second loop wire end extending forwardly from the operative end.

3. The catheter assembly according to claim 1, wherein a support for the second loop wire end comprises an attachment to the hollow catheter.

4. The catheter assembly according to claim 1, further comprising a support disposed on the hollow catheter and configured to support the second loop wire end, wherein the support for the second loop wire end is attached at the operative end of the hollow catheter.

5. The catheter assembly according to claim 1, wherein the hollow catheter further comprises a support configured to support the first loop wire end.

6. The catheter assembly according to claim 1, wherein the hollow catheter further comprises a plurality of channels that respectively incorporate the loop wire and a guide wire.

7. The catheter assembly according to claim 1, wherein at least one of (a) the control end of the hollow catheter or (b) the first loop wire end comprises a cooperative position indicator.

8. The catheter assembly according to claim 7, wherein the cooperative position indicator has an effective operation of at least two centimeters.

9. The catheter assembly according to claim 1, wherein a lumen of the hollow catheter is formed to permit contrast fluids to pass through the hollow catheter.

10. The catheter assembly according to claim 1, wherein said hollow catheter further comprises a dilatator.

11. The catheter assembly according to claim 5, wherein the first loop wire end is detachably attached to the hollow catheter.

12. The catheter assembly according to claim 1, further comprising a second loop wire that is exterior to the hollow catheter and maneuverable in relation thereto, the second loop wire being connected to the operative end and extending to the control end.

13. The catheter assembly according to claim 1, wherein the distal cutting edge portion consists of a single filament.

14. A catheter assembly, comprising:
   a hollow catheter having an operative end; and
   a loop wire moveably arranged with respect to the hollow catheter to form a cutting loop located forwardly of the operative end of the hollow catheter,
   wherein the cutting loop includes a distal cutting edge portion extending from the operative end of the hollow catheter, the distal cutting edge portion being positioned at a distal tip of the cutting loop at a forward most point of the catheter assembly, and
   wherein the loop wire is supported by the hollow catheter and arranged so that a pushing force from several grams to several hundred grams is exertable by the cutting loop at the distal cutting edge portion in a direction along a longitudinal axis of the hollow catheter to push aside and cut tissue within a vein or artery in the direction along the longitudinal axis of the hollow catheter when the cutting loop is longitudinally extended.

15. A catheter assembly for passing or bypassing an occlusion in veins or arteries, comprising:
   a hollow catheter having a distal operative end and a proximal control end and comprising a plurality of channels extending from the proximal control end to the distal operative end to respectively incorporate a loop wire and a guide wire;
   the loop wire, which extends through the hollow catheter, the loop wire having a first loop wire end and a second loop wire end, extending rearwardly to the proximal control end of the hollow catheter and a cutting loop extending forwardly from the distal operative end of the hollow catheter, the loop wire being arranged to be moved rearwardly and forwardly with respect to the hollow catheter to respectively diminish and enlarge a size of the cutting loop, and
   a cooperative position indicator arranged at the proximal control end of the hollow catheter to control an effective position of the loop wire with respect to the hollow catheter,
   wherein the cutting loop is arranged to cut or part tissue at a distal cutting edge portion positioned at a distal tip of the cutting loop in a direction along a longitudinal axis of the hollow catheter, and
   wherein a rigidity of the cutting loop is sufficient to exert a pushing force in a distal direction from several grams to several tens of grams.

16. The catheter assembly according to claim 15, wherein the cooperative position indicator has an effective operation of at least two centimeters.

17. The catheter assembly according to claim 15, wherein the cooperative position indicator comprises a scale gradation indicating the size of the cutting loop.

18. The catheter assembly according to claim 15, wherein a rigidity of the distal operative end of the hollow catheter is greater than the rigidity of the cutting loop such that upon encountering a load, the cutting loop deforms in preference to the distal operative end of the hollow catheter.

19. The catheter assembly according to claim 15, wherein one of the plurality of channels is a guide wire lumen, and the guide wire extends through the guide wire lumen.

* * * * *